(12) United States Patent
Black et al.

(10) Patent No.: US 10,617,450 B2
(45) Date of Patent: Apr. 14, 2020

(54) JOINTED ROD

(71) Applicant: GLOBUS MEDICAL, INC., Audubon, PA (US)

(72) Inventors: Michael Black, Swarthmore, PA (US); Michael Zentko, Lansdale, PA (US)

(73) Assignee: Globus Medical, Inc., Audubon, PA (US)

( * ) Notice: Subject to any disclaimer, the term of this patent is extended or adjusted under 35 U.S.C. 154(b) by 161 days.

(21) Appl. No.: 15/364,314

(22) Filed: Nov. 30, 2016

(65) Prior Publication Data

US 2017/0079691 A1      Mar. 23, 2017

Related U.S. Application Data

(63) Continuation of application No. 14/933,033, filed on Nov. 5, 2015, now Pat. No. 9,532,811, which is a continuation of application No. 13/083,267, filed on Apr. 8, 2011, now Pat. No. 9,204,901.

(60) Provisional application No. 61/322,023, filed on Apr. 8, 2010.

(51) Int. Cl.
 *A61B 17/70* (2006.01)

(52) U.S. Cl.
 CPC ...... *A61B 17/7055* (2013.01); *A61B 17/7004* (2013.01); *A61B 17/705* (2013.01); *A61B 17/7007* (2013.01); *A61B 17/7052* (2013.01)

(58) Field of Classification Search
 CPC .............. A61B 17/705; A61B 17/7037; A61B 17/7052

USPC ........................................................ 606/260
See application file for complete search history.

(56) References Cited

U.S. PATENT DOCUMENTS

| | | | | |
|---|---|---|---|---|
| 4,433,677 A | * | 2/1984 | Ulrich ................ | A61B 17/7055 606/250 |
| 5,312,405 A | * | 5/1994 | Korotko ............. | A61B 17/7052 606/252 |
| 5,515,744 A | * | 5/1996 | Liao ...................... | B62K 21/16 403/373 |
| 5,653,708 A | * | 8/1997 | Howland ........... | A61B 17/7041 606/264 |
| 5,947,967 A | * | 9/1999 | Barker ................ | A61B 17/7037 606/278 |
| 5,976,133 A | * | 11/1999 | Kraus .................. | A61B 17/171 606/54 |
| 6,007,536 A | * | 12/1999 | Yue ...................... | A61B 17/809 606/60 |
| 6,554,831 B1 | * | 4/2003 | Rivard ............... | A61B 17/7035 606/253 |
| 6,887,241 B1 | * | 5/2005 | McBride ............ | A61B 17/7049 606/252 |
| 7,485,132 B1 | * | 2/2009 | McBride ............ | A61B 17/7052 606/250 |

(Continued)

*Primary Examiner* — Jan Christopher L Merene

(57) ABSTRACT

The present invention is a spinal fixation device that includes an occipital rod having a first end and a second end, and a spinal rod extending from a connection housing having a first end and a second end. The first end of the spinal rod is integral with a portion of the connection housing and the connection housing is configured with an elongated opening, a rotating plug, and a locking mechanism. The elongated opening is configured for mating with the first end of the occipital plate and the locking mechanism is adapted to enable the occipital rod to be locked in a fixed position.

14 Claims, 9 Drawing Sheets

(56) References Cited

U.S. PATENT DOCUMENTS

| | | | | |
|---|---|---|---|---|
| 7,686,833 B1* | 3/2010 | Muhanna | A61B 17/7005 | 606/257 |
| 7,744,634 B2* | 6/2010 | Farris | A61B 17/7014 | 606/260 |
| 7,901,433 B2* | 3/2011 | Forton | A61B 17/7055 | 606/246 |
| 8,361,117 B2* | 1/2013 | Michielli | A61B 17/7049 | 606/250 |
| 9,597,122 B2* | 3/2017 | Sandhu | A61B 17/7055 | |
| 2002/0143330 A1* | 10/2002 | Shluzas | A61B 17/7052 | 606/252 |
| 2003/0114852 A1* | 6/2003 | Biedermann | A61B 17/645 | 606/253 |
| 2003/0171752 A1* | 9/2003 | Assaker | A61B 17/7037 | 606/250 |
| 2004/0133203 A1* | 7/2004 | Young | A61B 17/7052 | 606/253 |
| 2004/0215190 A1* | 10/2004 | Nguyen | A61B 17/1671 | 606/86 A |
| 2005/0228376 A1* | 10/2005 | Boomer | A61B 17/7013 | 606/260 |
| 2005/0228378 A1* | 10/2005 | Kalfas | A61B 17/7049 | 606/252 |
| 2006/0009766 A1* | 1/2006 | Lee | A61B 17/7052 | 74/1 R |
| 2006/0052785 A1* | 3/2006 | Augostino | A61B 17/7049 | 606/247 |
| 2006/0111715 A1* | 5/2006 | Jackson | A61B 17/861 | 128/897 |
| 2006/0217710 A1* | 9/2006 | Abdou | A61B 17/6433 | 606/54 |
| 2006/0229611 A1* | 10/2006 | Avery | A61B 17/7011 | 606/260 |
| 2007/0016193 A1* | 1/2007 | Ritland | A61B 17/7011 | 606/257 |
| 2007/0161988 A1* | 7/2007 | Drewry | A61B 17/7005 | 606/86 A |
| 2008/0021455 A1* | 1/2008 | Chao | A61B 17/7034 | 606/250 |
| 2008/0103507 A1* | 5/2008 | Purcell | A61B 17/7052 | 606/103 |
| 2008/0109039 A1* | 5/2008 | Michielli | A61B 17/7052 | 606/251 |
| 2008/0177260 A1* | 7/2008 | McKinley | A61B 17/7037 | 606/60 |
| 2008/0215095 A1* | 9/2008 | Biedermann | A61B 17/7031 | 606/246 |
| 2008/0234746 A1* | 9/2008 | Jahng | A61B 17/1757 | 606/278 |
| 2009/0018584 A1* | 1/2009 | Henderson, Sr. | A61B 17/7047 | 606/246 |
| 2009/0187217 A1* | 7/2009 | Weiman | A61B 17/7052 | 606/257 |
| 2009/0204156 A1* | 8/2009 | McClintock | A61B 17/7002 | 606/278 |
| 2010/0030224 A1* | 2/2010 | Winslow | A61B 17/7005 | 606/104 |
| 2010/0094302 A1* | 4/2010 | Pool | A61B 17/7004 | 606/90 |
| 2010/0094345 A1* | 4/2010 | Saidha | A61B 17/7052 | 606/250 |
| 2010/0114167 A1* | 5/2010 | Wilcox | A61B 17/7004 | 606/250 |
| 2010/0160971 A1* | 6/2010 | Glerum | A61B 17/7037 | 606/278 |
| 2011/0087287 A1* | 4/2011 | Reeder, Jr. | A61B 17/7011 | 606/250 |
| 2011/0098748 A1* | 4/2011 | Jangra | A61B 17/7004 | 606/278 |
| 2011/0110712 A1* | 5/2011 | Richelsoph | A61B 17/7052 | 403/192 |
| 2011/0251645 A1* | 10/2011 | Black | A61B 17/7004 | 606/264 |
| 2011/0270314 A1* | 11/2011 | Mueller | A61B 17/704 | 606/264 |
| 2012/0010663 A1* | 1/2012 | Black | A61B 17/7052 | 606/279 |
| 2015/0257793 A1* | 9/2015 | Baynham | A61B 17/7041 | 606/278 |

* cited by examiner

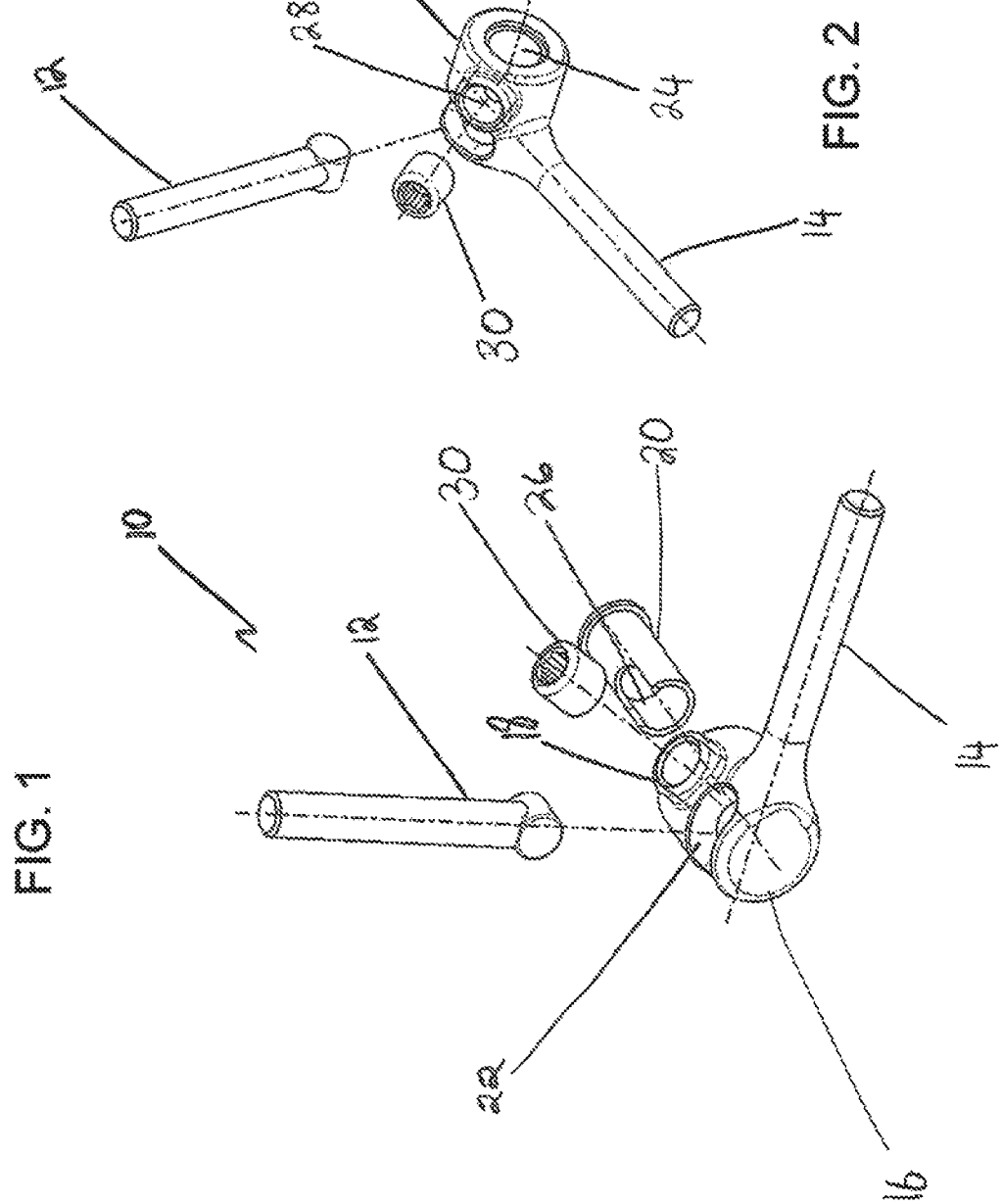

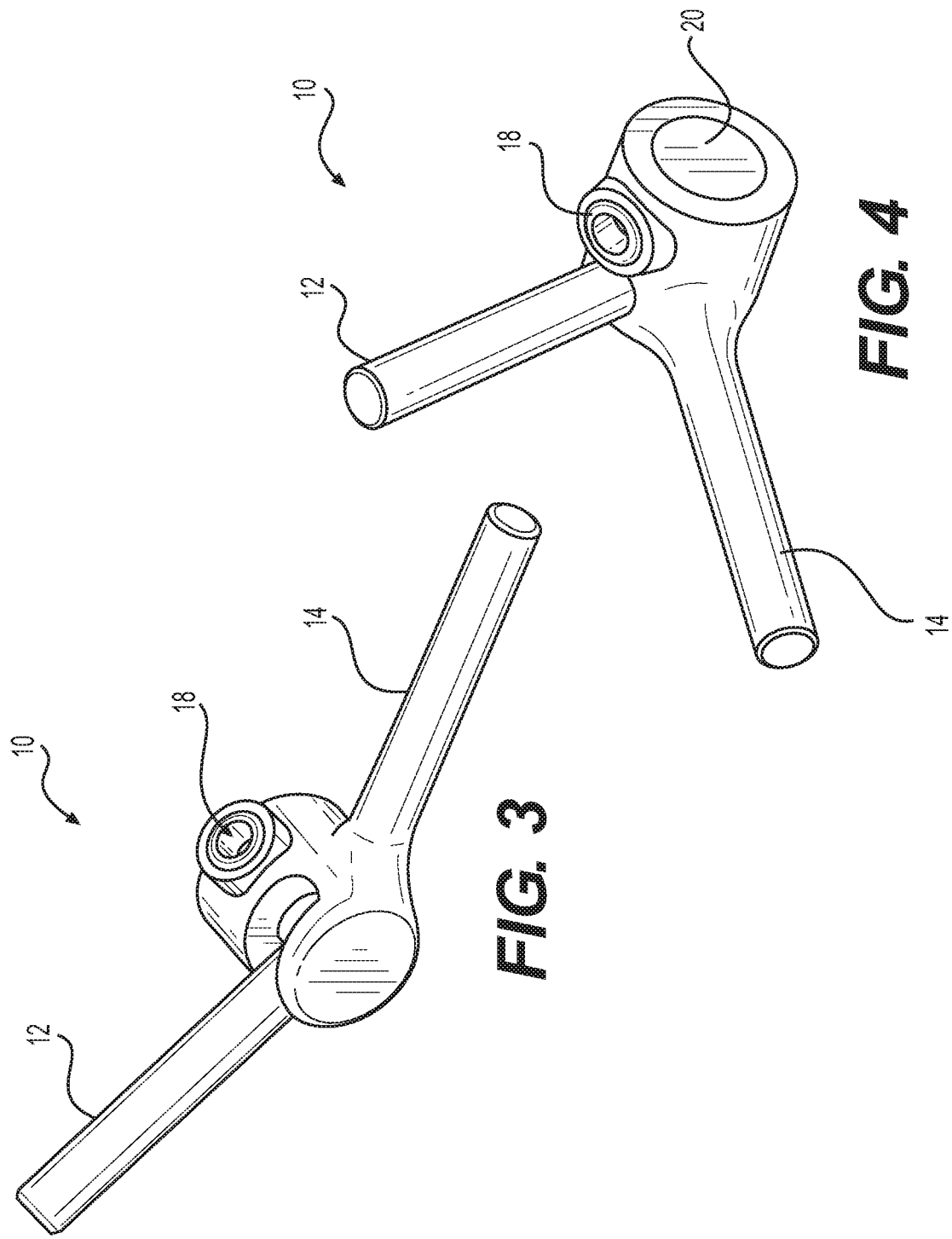

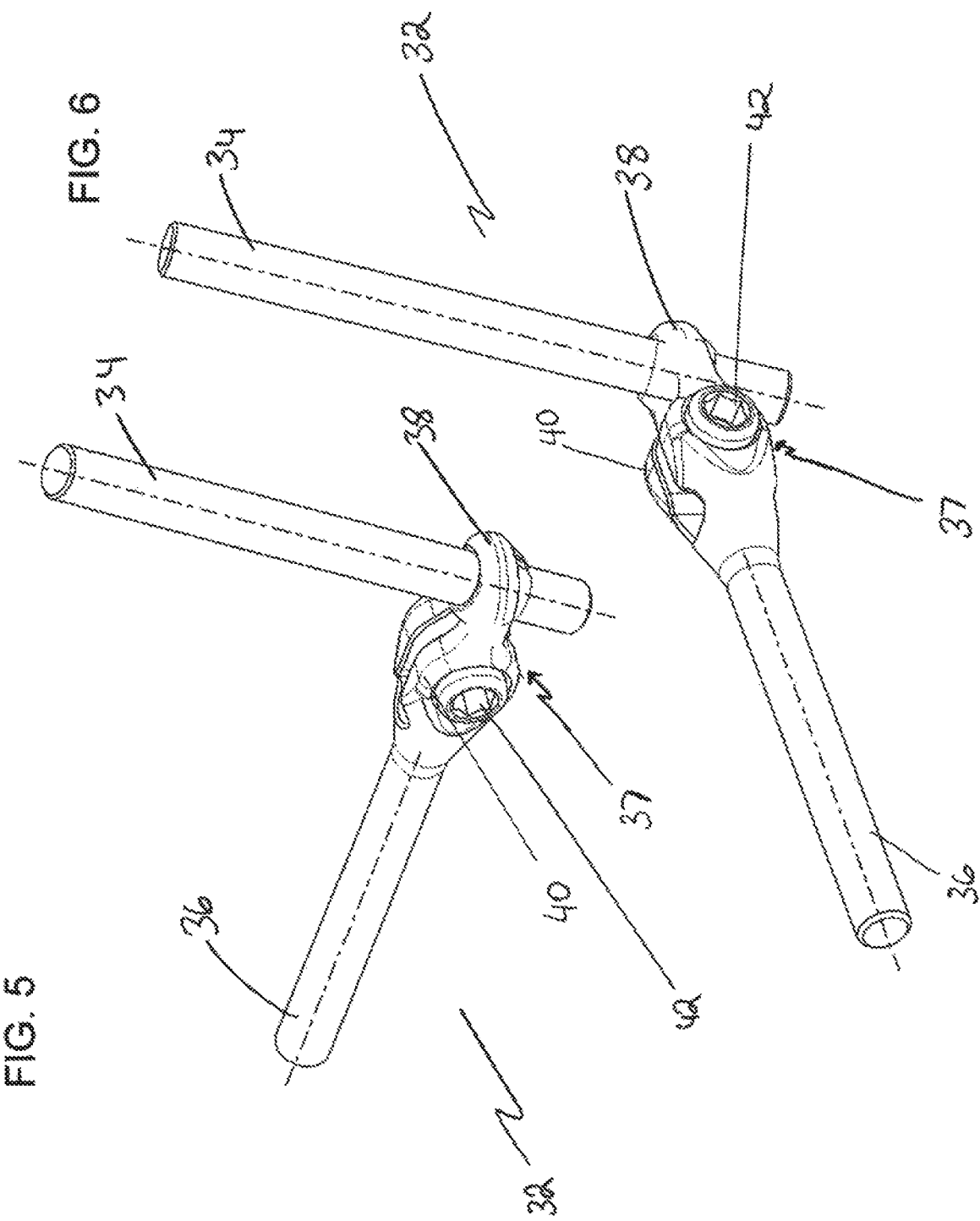

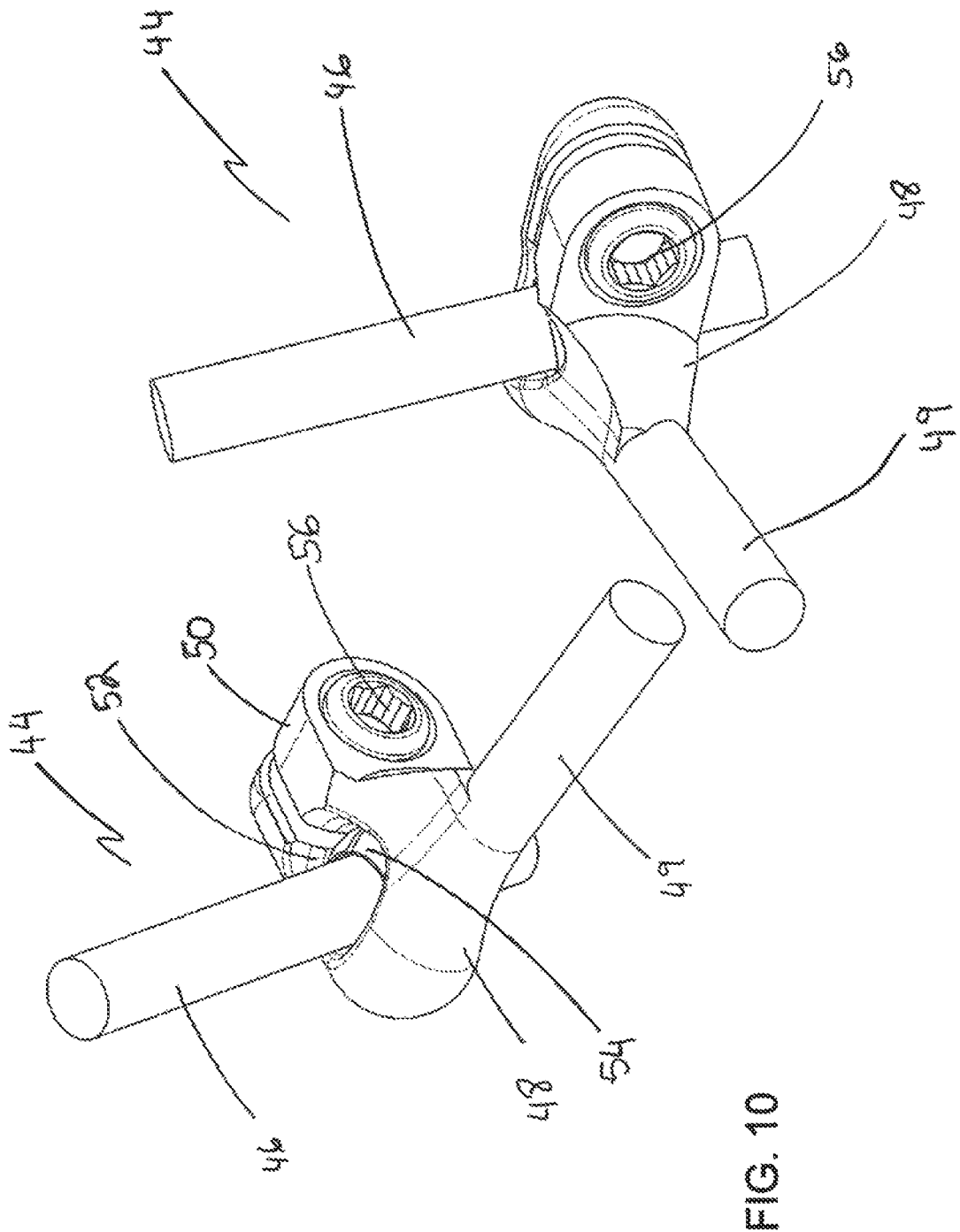

JOINTED ROD

CROSS-REFERENCE TO RELATED APPLICATIONS

This application is a continuation application which claims priority to U.S. patent application Ser. No. 14/933,033, filed Nov. 5, 2015, which claims priority to U.S. patent application Ser. No. 13/083,267, filed Apr. 8, 2011, now U.S. Pat. No. 9,204,901, which is a non-provisional application that claims priority to provisional application Ser. No. 61/322,023 filed on Apr. 8, 2010, each of which is hereby incorporated by reference in its entirety.

FIELD OF THE INVENTION

The present disclosure generally relates to a fixation device for positioning and immobilizing at least two adjacent vertebrae.

BACKGROUND

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses. Typically, weaknesses in the spine are corrected by using devises that fuse one or more vertebrae together.

One method of correcting the weaknesses in the spine is to use a posterior cervical fixation system that does not only include spinal level fusion, but can also include fusion to the occipital bone on the back of the skull. In order to connect spinal rods to the occipital bone on the skull from the spinal column, surgeons can either bend straight spinal rods to meet the occipital contours and angles or further bend a pre-bent spinal rod, where the spinal rod can be provided in multiple pre-bent angles. However, contouring the spinal rod to meet the desired angles and contours can be a difficult and time consuming process. There is a need for an improved posterior cervical fixation system that can be easily installed and adjusted.

SUMMARY OF THE INVENTION

The present invention is a spinal fixation device that includes an occipital rod having a first end and a second end, and a spinal rod extending from a connection housing having a first end and a second end. The first end of the spinal rod is integral with a portion of the connection housing and the connection housing is configured with an elongated opening, a rotating plug, and a locking mechanism. The elongated opening is configured for mating with the first end of the occipital plate and the locking mechanism is adapted to enable the occipital rod to be locked in a fixed position.

BRIEF DESCRIPTION OF THE DRAWINGS

The invention will be more fully understood from the following detailed description taken in conjunction with the accompanying drawings, in which:

FIGS. 1 and 2 are exploded views of a hinged spinal rod system according to one embodiment of the present invention.

FIGS. 3 and 4 are views of the assembled hinged spinal rod system illustrated in FIGS. 1 and 2.

FIG. 5 is a side view of a hinged spinal rod system according to another embodiment of the present invention.

FIG. 6 is a top view of the hinged spinal rod system according to the present invention.

FIGS. 10 and 11 are perspective views of another embodiment of a hinged spinal rod system according to the present invention.

DETAILED DESCRIPTION OF THE ILLUSTRATED EMBODIMENTS

Figure 7:
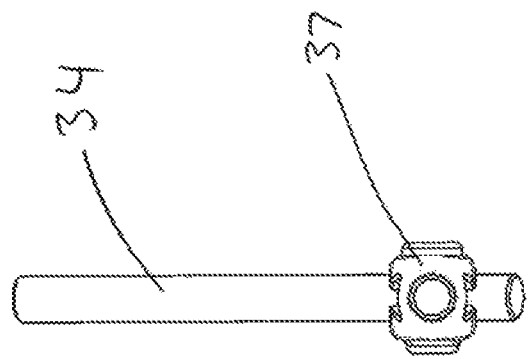
FIG. 7 is a front view of the hinged spinal rod system according to the present invention.
Figure 8:
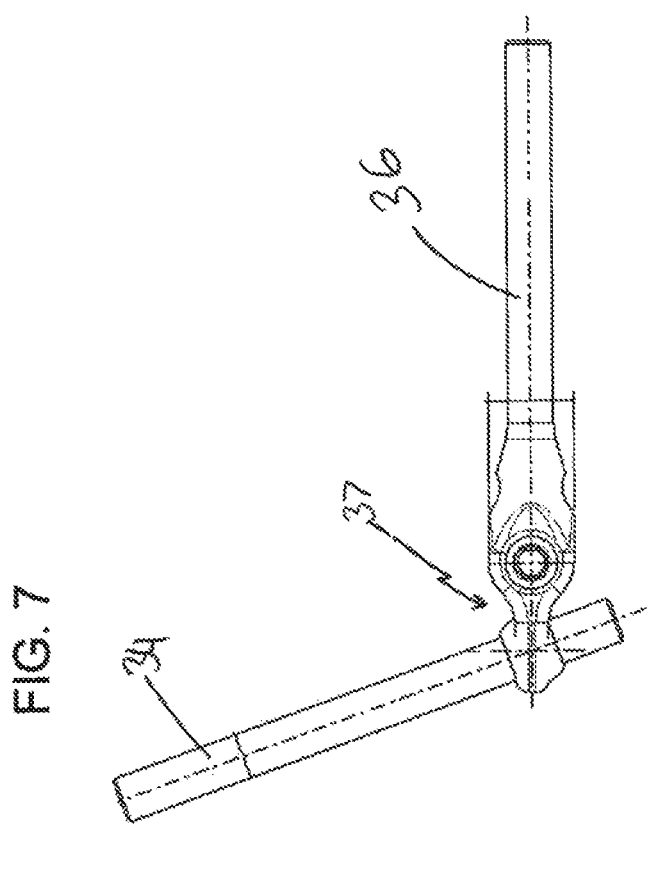
FIGS. 8 and 9 are perspective views of the hinged spinal rod system according to the embodiment illustrated in FIGS. 5-7.
Figure 9:
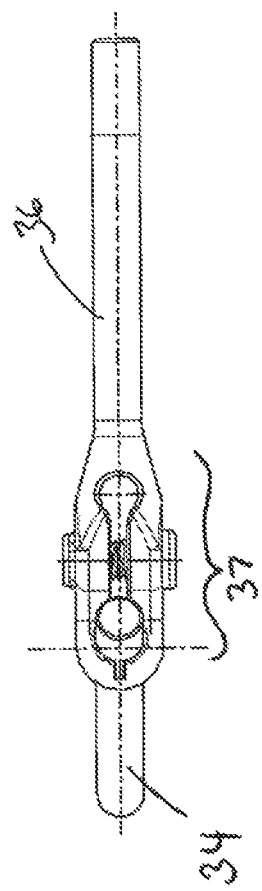
Figure 12:
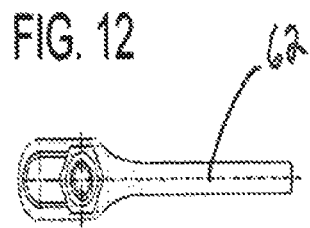
FIGS. 12-16 illustrate yet another embodiment of a hinged spinal rod system according to the present invention.
Figures 13, 14:
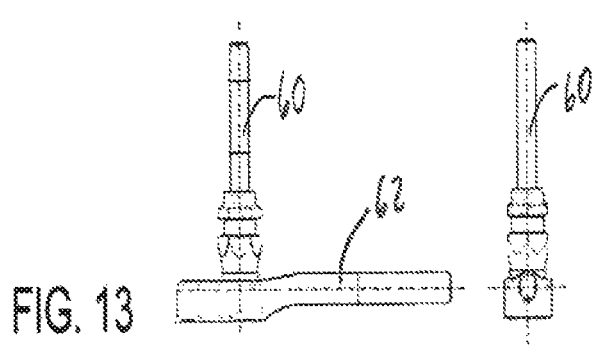
Figure 15:
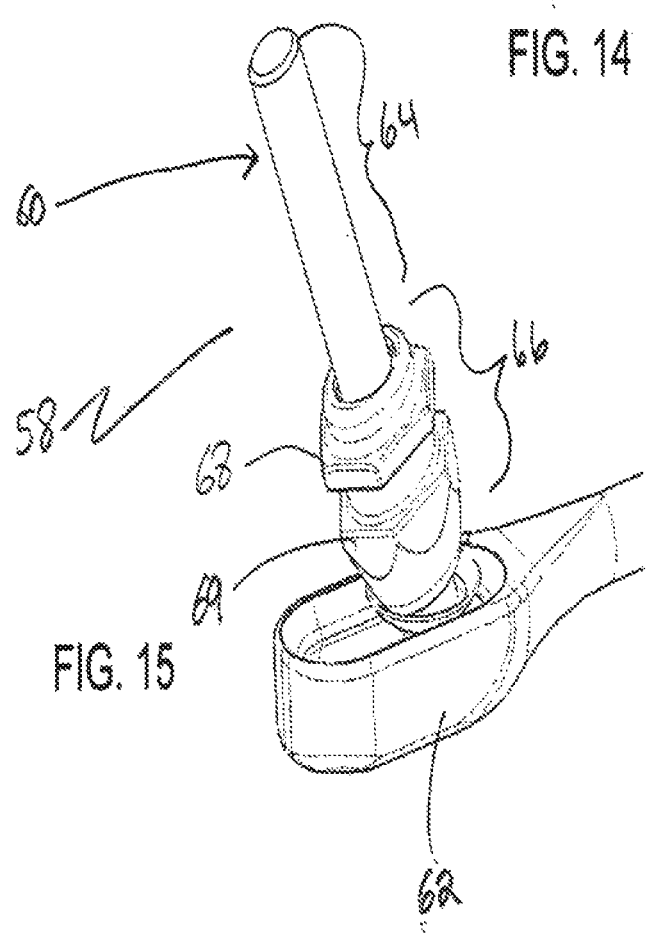
Figure 16:
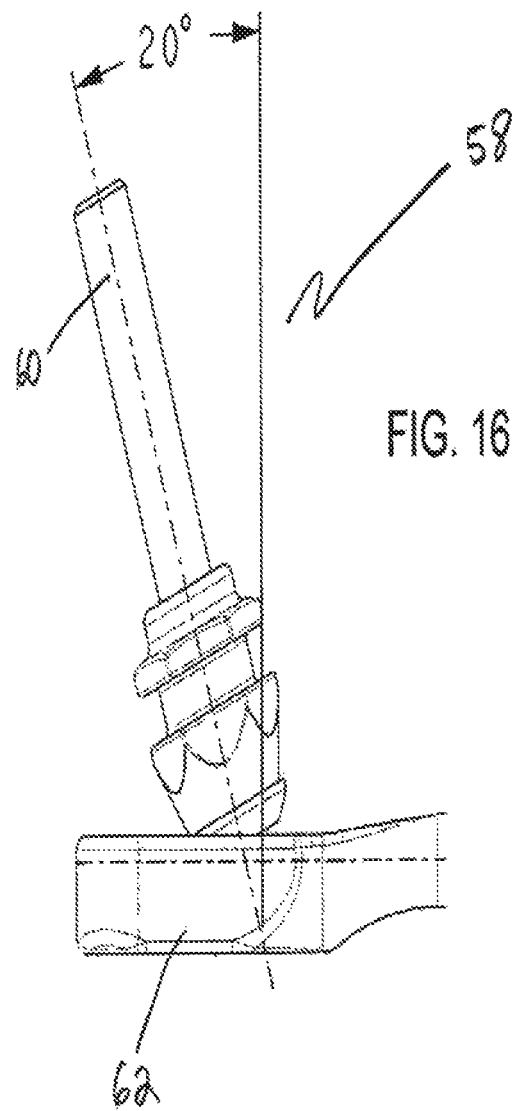

The following description of the preferred embodiment(s) is merely exemplary in nature and is in no way intended to limit the invention, its application, or uses.

FIGS. 1-19 illustrate different embodiments of a jointed or hinged spinal rod system that provides various angularly adjustable spinal fixation devices. The systems also provide the flexibility to position and contour spinal rods to alleviate the majority of complications that can arise when trying to complete an occipital fusion. The systems generally include an occipital rod, a spinal rod, a housing having a locking mechanism that couples the occipital rod and the spinal rod in a fixed position.

FIGS. 1-4 illustrate a preferred embodiment of a hinged or jointed rod system 10. The hinged rod system 10 includes a pivoting occipital rod 12, a spinal rod 14 integrated with a housing 16, a locking mechanism 18, and a pivoting locking plug 20. The system 10 is configured to allow for the occipital rod 12 to pivot angularly relative to the spinal rod 14 and the housing 16. The occipital rod 12 is an elongated member that is provided with a first end and a second end. The first end is configured to be received within the housing 16. The second end is configured to be received within a bone fixation device, such as a bone screw, a plate, or a hook type device. The spinal rod 16 is also provided with a first end and a second end. The first end of the spinal rod is integral with the housing 16. In one embodiment, the first end of the spinal rod 14 can be offset and attached to the housing in different configurations.

The spinal rod 14 may also be contoured and adjusted to pedicle screws, hooks, clamps, bone plates and other such devices to enable fixation of adjacent vertebrae. The occipital rod 12 and the spinal rod 14 can each have any shape or size, and each rod can vary in diameter relative to one another. The rods can also vary in length depending on the indented use. In the preferred embodiment, the rods are substantially cylindrical rods.

The housing 16 includes the locking mechanism 18, the pivoting locking plug 20 and an elongated opening 22. The elongated opening 22 is configured to receive the first end of the occipital rod 12 and designed to enable the occipital rod to move 90° in the cephalad-caudal direction with respect spinal rod 14 and the housing 16. The pivoting locking plug 20 is fitted within the housing 16 through an opening 24 and is provided with an elongated cutout 26. The elongated cutout 26 is positioned so that it corresponds with the elongated opening 22. Turning to the assembled views of the system 10, as shown in FIGS. 3 and 4, the occipital rod 12 is laser welded to the pivoting locking plug 22 to provide additional strength and rigidity to the spinal fixation system. As a result, as the plug is capable of rotating, the spinal rod 12 can also be pivoted accordingly.

The occipital rod 12 is received within the elongated cutout 26 of the pivoting locking plug 20 and can rotate the length of the elongated opening 22. The pivoting locking plug 20 pivots and moves with the occipital rod 12 and provides support for the occipital rod 12 in the housing 16, thereby reducing any "play" or unnecessary movement within the housing 16. The plug also prevents the occipital rod from exiting the housing through the elongated opening 22.

The system 10 also includes a locking mechanism 18 that is adapted to lock the occipital rod 12 in a fixed position relative to the spinal rod 14 and the housing 16. It should be noted that while any technique can be used to lock the occipital rod 12 in a fixed position, FIGS. 1-4 illustrate an exemplary embodiment of a locking mechanism 18. In this embodiment, the housing 16 is provided with a screw hole 28 which is configured to receive a set screw 30. The set screw 30 is used to lock the pivoting locking plug 20 by compressing upon the outer surface of the plug 20 within the housing 16 thereby fixing the occipital rod 12. The locking set screw 30 locks the occipital rod 12 in place once the desired angulation of the occipital rod 12 with respect to the spinal rod 14 is achieved. The locking set screw 18 is turned until it abuts the locking plug 20 preventing the locking plug 20 from pivoting or rotating. This, in turn, prevents the occipital rod 12 from pivoting. Although in the preferred embodiment, a locking set screw 30 is used to fasten the pivoting rod to the housing 16, it should be known that any fastening means that may fix the pivoting rod to the housing 16 may be used. Specifically, in the preferred embodiment, a threaded set screw configuration is utilized as a locking mechanism, however, any locking mechanism such as a pin, a clamp or cam-type system may be applied as a comparable locking mechanism.

Now turning to FIGS. 5-9, another embodiment of the hinged spinal rod system 32 is shown. The hinged spinal rod system 32 includes a first elongated spinal rod 34 and a second elongated spinal rod 36 and a connecting element 37. The connecting element 37 is comprised of a rod receiving element 38 and a clamping element 40. The first elongated spinal rod 34 is received within the connecting element 37 through an opening in the rod receiving element 38 of the connecting element 37. The rod receiving element 38 is also provided with a bushing within the opening which enables the angulation of the first elongated spinal rod 34. The second elongated spinal rod 36 is integral with the connecting element 37. Also, as illustrated in FIGS. 5-9, the rod receiving element 38 is integrally connected to the connecting element 37. The clamping element 40 is provided with a bore that is configured to receive a clamping screw 42. As the clamping screw 42 is tightened, the rod receiving element 38 is compressed thereby locking the first elongated spinal rod 34 within the rod receiving element 38. It should be noted that before the clamping screw 42 is tightened, first elongated spinal rod 34 is angulated to be set in an optimal position. Once the desired position of the spinal rod 34 is determined, the clamping screw 42 is tightened, thereby locking the first elongated spinal rod 34 into a fixed position.

FIGS. 10 and 11 are yet another embodiment of a hinged spinal rod system 44 according the present invention. In this embodiment, the hinged spinal rod system 44 includes a first elongated spinal rod 46, a connecting element 48, and a second elongated spinal rod 49 that is integral with the connecting element 48. The connecting element 48 is provided with a clamping element 50 and a rod receiving bore 52. The rod receiving bore 52 is configured to receive the first elongated spinal rod 46 within a bushing 54. The bushing 54 enables the angulation of the first elongated spinal rod 46 within the rod receiving bore 52. The clamping element 50 is configured to receive a clamping screw 56 which when tightened compresses the bushing 54, thereby fixing the first elongated spinal 48 into a desired position. It should be noted that although a clamping screw 56 is used to tighten the clamping element 50, any mechanism to tighten the clamp to lock the first elongated spinal 46 rod may be used.

FIGS. 12-16 are views of another embodiment of a hinged spinal rod system 58 according to the present invention. In this embodiment, the hinged spinal rod system 58 includes an elongated spinal rod 60, and a slotted base rod 62. The elongated spinal rod 60 is configured with a first portion 64 and a second portion 66. The first portion 64 is configured to attach to an occipital plate, a screw, hook and any comparable fixation device. The second portion 66 of the elongated spinal rod 60 is provided with a washer 68, and a locking nut 69. The second portion 66 of the elongated rod 60 is configured to couple with the slotted base rod 62. The elongated rod 60 may be translated within the slotted base rod 62 and provides for angulation based on the anatomy and design requirements for the fixation of adjacent vertebrae. The slotted base rod 62 is configured with a slot portion and an extended rod portion. The slot portion is configured to receive the second portion of the elongated spinal rod 60. The extended rod portion is configured to couple to a spinal plate, a pedicle screw, hooks, and any other comparable type spinal device. The elongated spinal rod 60 is locked within the slotted base rod 62 through a threaded portion 66 on the second portion. The threaded second portion engages with threads located within the portion of the base of the slotted base rod 62.

Figure 17:
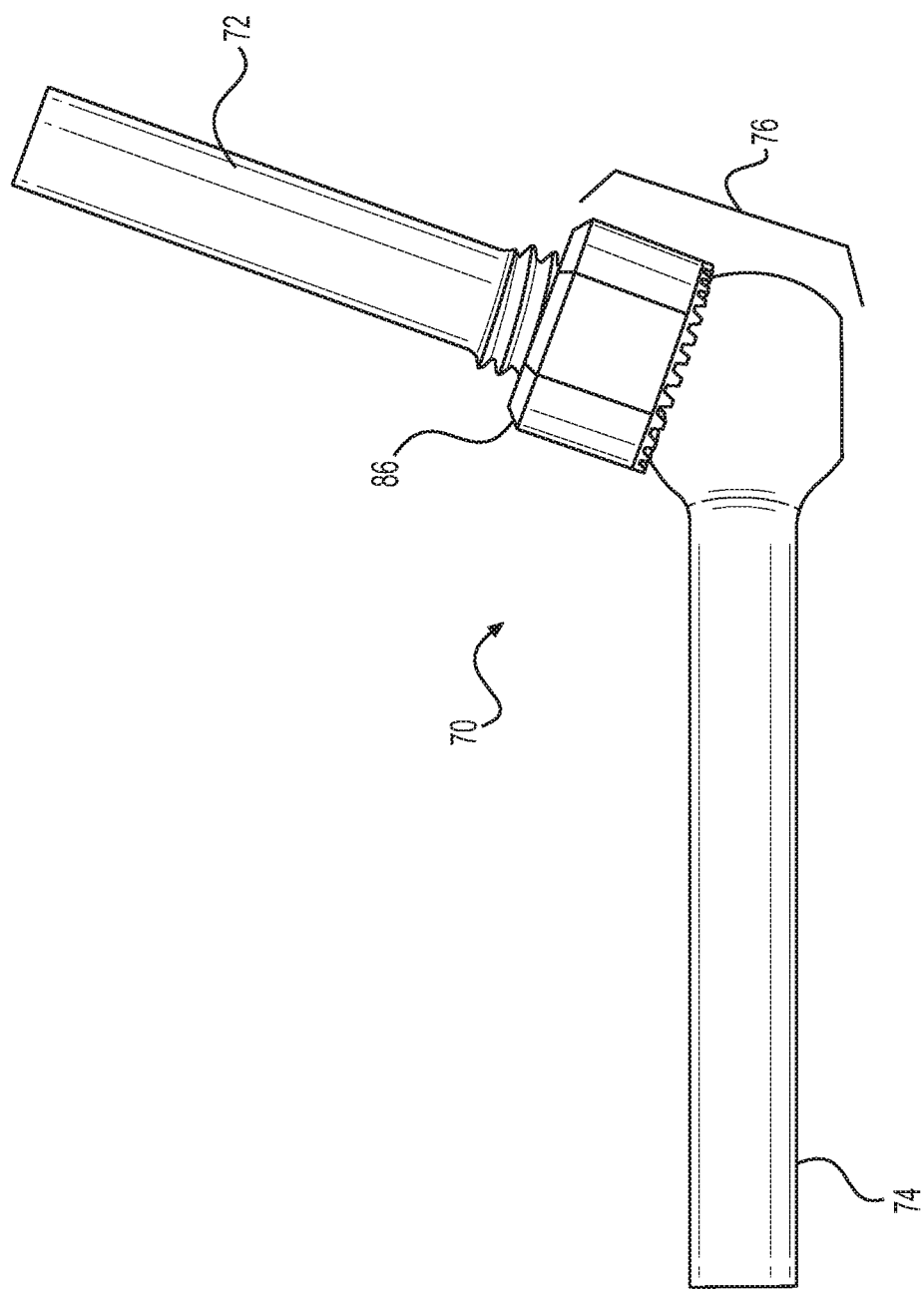
FIGS. 17-19 illustrate yet another embodiment of a hinged spinal rod system according to the present invention.
Figure 18:
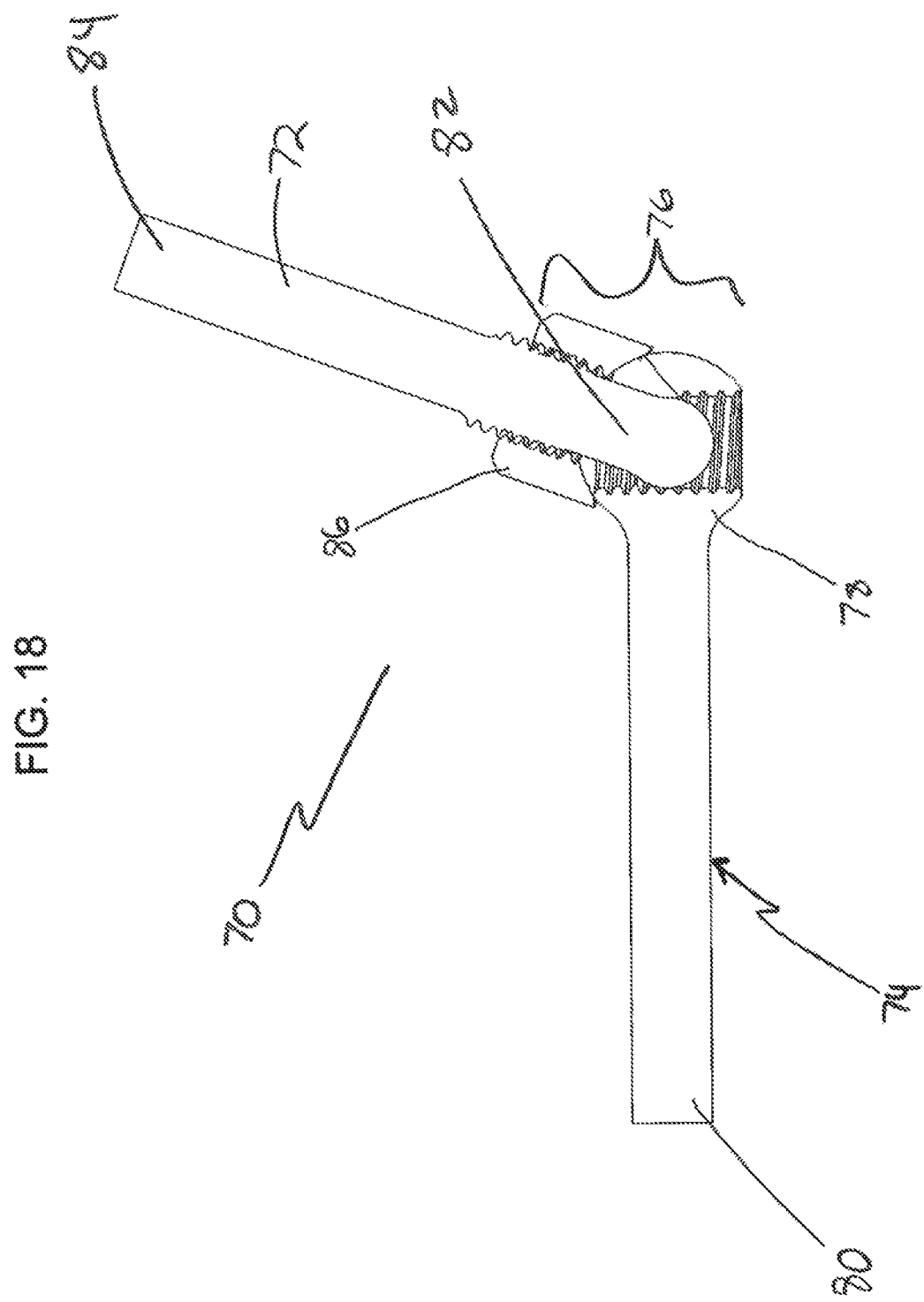
Figure 19:
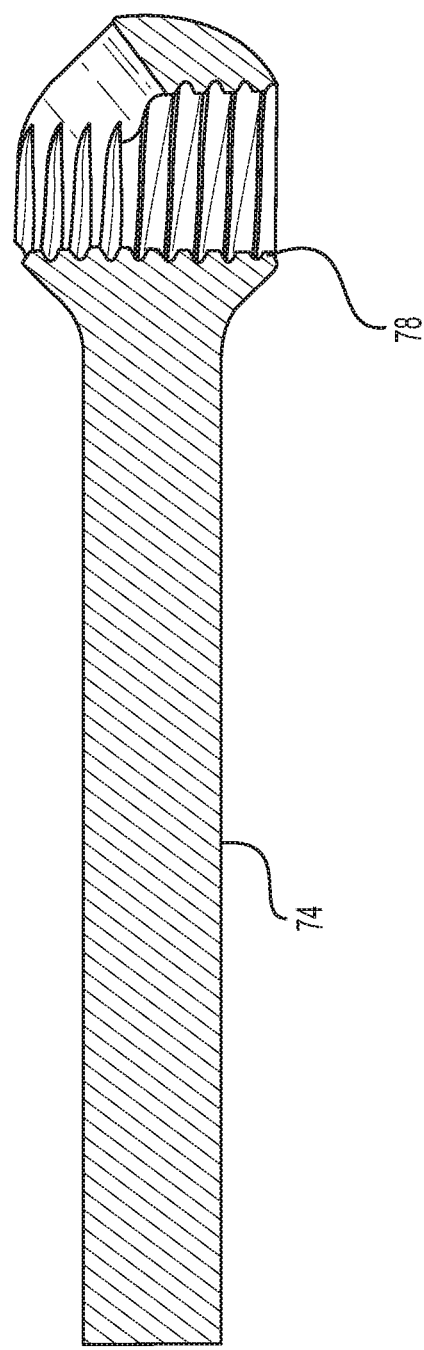

FIGS. 17-19 illustrate yet another embodiment of a hinged spinal rod system 70 according to another aspect of the present invention. The hinged spinal rod system 70 includes an elongated pivoting spinal rod 72, a fixed spinal rod 74, and a connecting element 76. The fixed spinal rod 74 is configured with a first end 78 and a second end 80. The first end 78 is spherical and is adapted to be coupled to the connected element 76. The connecting element 76 is adapted to be rotatable and pivotable relative to the second end 80 of the fixed spinal rod 74. The elongated pivoting spinal rod 72 is also provided with a first end 82 and a second end 84. The first end 82 of the pivoting spinal rod is coupled to the connected element 78. In one embodiment, the first end 82 of the pivoting spinal rod 72 is threaded and mates with the internal threading of the connecting element 76. The second end 84 of the pivoting spinal rod 72 is adapted to be received by an occipital plate, bone screws and other comparable fixation devices.

The fixed spinal rod 74 has a slot to control the angulation of the pivoting spinal rod 72 and minimize the medial-lateral rotation at the top portion. A surrounding element encloses or surrounds the slot to increase the overall stability of the construct. Once the pivoting spinal rod 72 is threaded through the fixed spinal rod 74, it is augmented to prevent it from unthreading. The connecting element 76 includes a locking nut 86 that includes a countered bottom surface that mate with the fixed spinal rod 74. As the locking nut 86 is actuated, it seats itself on the top surface of the fixed spinal rod 74 and puts the pivoting spinal rod 72 under a tensile force.

The hinged rod system 70 enables a titanium rod construct to function as a freely angulating hinge until it is locked with a locking mechanism such as the locking nut 86. In a preferred embodiment, the hinged mechanism of the present invention allows for in-situ adjustment of the rod construct. As a result, less time may be spent by the surgeon in adjusting and positioning the rod construct on the spine.

While it is apparent that the invention disclosed herein is well calculated to fulfill the objects stated above, it will be appreciated that numerous modifications and embodiments may be devised by those skilled in the art.

The invention claimed is:

1. A spinal fixation device comprising:
a first spinal rod having a central longitudinal axis;
a second spinal rod having a central longitudinal axis; and
a connecting element adapted to couple to the first and second spinal rod such that the central longitudinal axis of the first rod intersects with the central longitudinal axis of the second rod, the connecting element being monolithic with the second spinal rod;
wherein the connecting element includes a rod receiving element and a bushing and is configured for angulation of at least one of the first and second spinal rods,
wherein the first spinal rod is pivotable with respect to the second spinal rod,
wherein the first spinal rod pivots transversely to a longitudinal axis of the second spinal rod, and
wherein the first spinal rod and the second spinal rod are non-threaded, and wherein one end of the first spinal rod is directly coupled to an occipital plate.

2. The spinal fixation device of claim 1, wherein one end of the second spinal rod is coupled to a pedicle screw.

3. The spinal fixation device of claim 1, wherein the connecting element comprises a clamping element.

4. The spinal fixation device of claim 1, wherein the connecting element further comprises an opening for receiving the first spinal rod.

5. The spinal fixation device of claim 4, wherein the bushing is received within the opening, the bushing surrounding a portion of the first spinal rod.

6. The spinal fixation device of claim 3, wherein the connecting element includes a locking mechanism.

7. The spinal fixation device of claim 6, wherein the locking mechanism is a set screw that when tightened compresses the clamping element to fix the position of the first spinal rod.

8. A spinal fixation device comprising:
an occipital rod having a first end, a second end and a central longitudinal axis; and
a spinal rod extending from a connection housing having a first end, a second end and a central longitudinal axis, the first end of the spinal rod being monolithic with a portion of the connection housing;
wherein the connection housing is configured with a rod receiving element, a bushing, a clamping element and a locking mechanism,
wherein the locking mechanism being adapted to enable the occipital rod to be locked in a fixed position with respect to the spinal rod,
wherein the central longitudinal axis of the occipital rod intersects the central longitudinal axis of spinal rod when the spinal rod and the occipital rod are coupled through the connection housing,
wherein the occipital rod is configured to be pivoted with respect to the spinal rod,
wherein the occipital rod pivots transversely to a longitudinal axis of the spinal rod, and
wherein the occipital rod and the spinal rod are non-threaded, and wherein the second end of the occipital rod is directly coupled to an occipital plate.

9. The spinal fixation device of claim 8, wherein the second end of the spinal rod is coupled to a pedicle screw.

10. The spinal fixation device of claim 8, wherein the rod receiving element includes an opening and the bushing is received in the opening of the rod receiving element and is capable of moving in the opening.

11. The spinal fixation device of claim 10, wherein the bushing includes an opening that surrounds at least a portion of the occipital rod.

12. The spinal fixation device of claim 8, wherein the locking mechanism for locking the occipital rod in a fixed position comprises a set screw locking mechanism.

13. The spinal fixation device of claim 8, wherein the rod receiving element is integrally connected to the clamping element.

14. The spinal fixation device of claim 12, wherein the locking mechanism is a set screw that when tightened compresses the clamping element to fix the position of the occipital rod.

* * * * *